United States Patent [19]

Cragoe, Jr.

[11] 4,296,237

[45] Oct. 20, 1981

[54] 4-(PYRIDYL, PIPERAZINYL AND THIAZOLYL SUBSTITUTED THIAZOLYL)-3-HYDROXY-3-PYRROLINE-2,5-DIONES

[75] Inventor: Edward J. Cragoe, Jr., Lansdale; Clarence S. Roony, Worcester, both of Pa.

[73] Assignee: Merck & Co., Inc., Rahway, N.J.

[21] Appl. No.: 74,466

[22] Filed: Sep. 11, 1979

[51] Int. Cl.³ ............... C07D 417/14; A61K 31/425; A61K 31/44; A61K 31/495
[52] U.S. Cl. ................... 544/405; 546/284; 548/202
[58] Field of Search ............... 548/203, 202; 546/284; 544/405; 424/270

[56] References Cited

U.S. PATENT DOCUMENTS 3,340,263  9/1967  Stachlein et al.

OTHER PUBLICATIONS

Liao et al., Arch. Biochem. Biophys., 154, pp. 68–75, (1973).
Harlay, J. Pharm. Chim., 24, pp. 537–548, (1936).
Randall et al., J. Med. Chem., 22, pp. 608–614 (1979).
G. S. Skinner et al., J. Am. Chem. Soc., 73, pp. 2230–2233, (1951).
G. S. Skinner et al., J. Am. Chem. Soc., 70, pp. 4011–4013, (1948).

*Primary Examiner*—Donald G. Daus
*Assistant Examiner*—D. B. Springer
*Attorney, Agent, or Firm*—Raymond M. Speer; Michael C. Sudol, Jr.

[57] ABSTRACT

Novel 4-(substituted thiazolyl)-3-hydroxy-3-pyrroline-2,5-diones are disclosed which inhibit glycolic acid oxidase and thus are useful in the treatment and prevention of calcium oxalate renal lithiasis.

5 Claims, No Drawings

4-(PYRIDYL, PIPERAZINYL AND THIAZOLYL SUBSTITUTED THIAZOLYL)-3-HYDROXY-3-PYRROLINE-2,5-DIONES

BACKGROUND OF THE INVENTION

Close to 70% of kidney stones in man are composed partially or predominantly of calcium oxalate. There is no satisfactory drug specific for the treatment of calcium oxalate renal lithiasis, nor for prophylactic use by patients prone to recurrent attacks of this disease.

The most common treatment for renal lithiasis due to calcium oxalate consists of surgical removal of stones, control of the diet to restrict calcium or oxalate, and ingestion of large quantities of water to dilute the urine. Attempts at chemotherapy have included the administration of magnesium oxide, calcium carbimide, orthophosphate, cellulose phosphate, isocarboxazide, thiazide diuretics, allopurinol and succinimide. Limited success has been realized by these drug approaches. No drug which specifically inhibits the biosynthetic formation of oxalic acid has previously been developed for the treatment of calcium oxalate renal lithiasis.

The immediate metabolic precursor of the majority of the oxalate in the urine of a typical patient is glyoxylic acid. In turn its most important precursor is glycolic acid. The enzyme glycolate oxidase is able to carry out the oxidation of glycolic acid, through glyoxylic acid, to oxalic acid. Inhibition of this enzyme will, therefore, reduce the concentration of oxalic acid in the kidney and bladder, reducing the probability that calcium oxalate crystallization will occur. Thus inhibitors of glycolate oxidase provide a specific approach to the prevention and treatment of calcium oxalate renal lithiasis.

Liao, et al, *Arch. Biochem. Biophys.*, 154, 68–75 (1973) have shown that phenyllactic acid and n-heptanoic acid, which are inhibitors of glycolate oxidase, inhibit oxalate biosynthesis in isolated perfused rat liver. These compounds are not sufficiently potent to be useful as drugs.

The preparation of 3-hydroxy-4-phenyl-3-pyrroline-2,5-dione

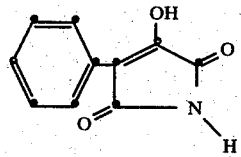

has been described by Harlay, *J. Pharm. Chim.*, 24, 537–48 (1936). 3-Hydroxy-4-aryl-3-pyrroline-2,5-diones are described in U.S. Pat. No. 3,349,263 as intermediates in the preparation of antiphlogistic substances. A number of 3-hydroxy-4-substitutedphenyl-3-pyrroline-2,5-diones are reported by G. S. Skinner et al., *J. Am. Chem. Soc.*, 73, 2230 (1951). (In this paper these compounds are referred to as pyrrolidine-2,3,5-trione derivatives). 3-Hydroxy-4-(4-bromo-1-naphthyl)-3-pyrroline-2,5-dione is described by G. S. Skinner et al., *J. Am. Chem. Soc.*, 70, 4011 (1948).

SUMMARY OF THE INVENTION

It has now been found that novel compounds of the formula:

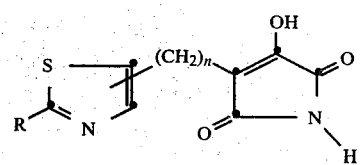

wherein
n is 0 to 2;
R is;

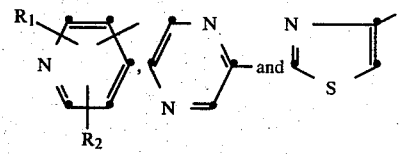

wherein
$R_1$ and $R_2$ on the pyridine ring are independently hydrogen, loweralkyl containing 1 to 4 carbons or halogen and pharmaceutically acceptable salts thereof, are potent inhibitors of glycolate oxidase. They are, therefore, useful in the treatment and prevention of calcium oxalate kidney and bladder stone formation.

Preferred compounds are those wherein n is 0 having the structure:

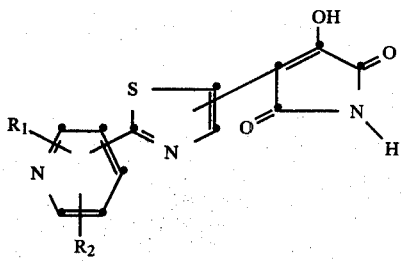

wherein
$R_1$ and $R_2$ are independently hydrogen, halogen or loweralkyl containing 1 to 4 carbons.

Still further preferred compounds are those wherein $R_1$ and $R_2$ are hydrogen having the structure:

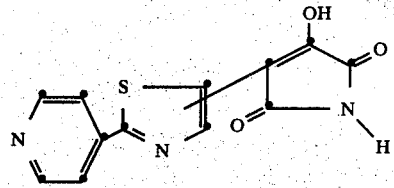

Still further preferred compounds are those having the structure:

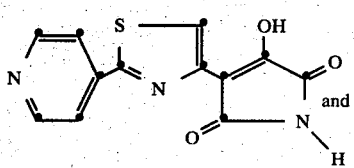

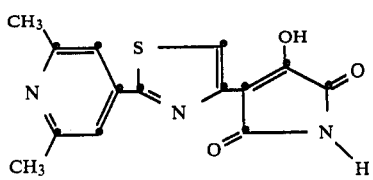

DETAILED DESCRIPTION

About 70% of all renal calculi contain oxalate as the main component of the matrix. In the majority of patients the condition is associated with a higher than average level of metabolically produced oxalate. The major pathway for biosynthesis of oxalate can be represented as follows:

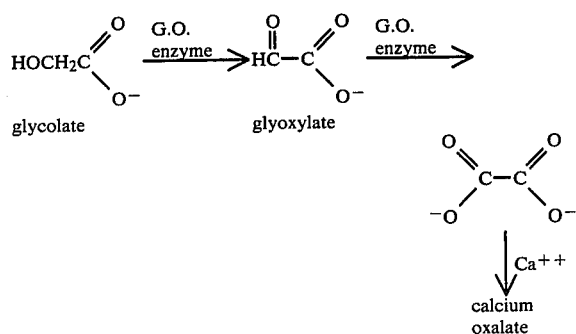

Glyoxylate is the major immediate forerunner of oxalate. An inhibitor of glycolate oxidase (G.O.) will inhibit both the conversion of glyoxylate to oxalate as well as the production of glyoxylate from glycolate. By reducing oxalic acid levels in the urine with the compounds of this invention, the formation of oxalate calculi will be reduced or prevented.

Compounds of formula (I) are potent inhibitors of glycolate oxidase and thus are useful in restricting oxalate levels in the blood and urine. Further, they are useful in the treatment and prevention of renal disease due to calcium oxalate stone formation in the kidney and bladder. They may be useful in the treatment of the genetically inherited diseases termed Hyperoxaluria types I and II in which very high levels of metabolic oxalic acid are present.

Compounds of formula (I) have been unexpectedly found to block the contractions of guinea pig ileum induced by Slow Reacting Substance of Anaphylaxis (SRS-A). They are ineffective against contractions caused by histamine, which demonstrates specificity against SRS-A. SRS-A is considered a major mediator in human allergic asthma. Thus the compounds of formula (I) are useful in the treatment of allergy, especially allergic asthma.

Compounds of formula (I) can be prepared according to the following scheme:

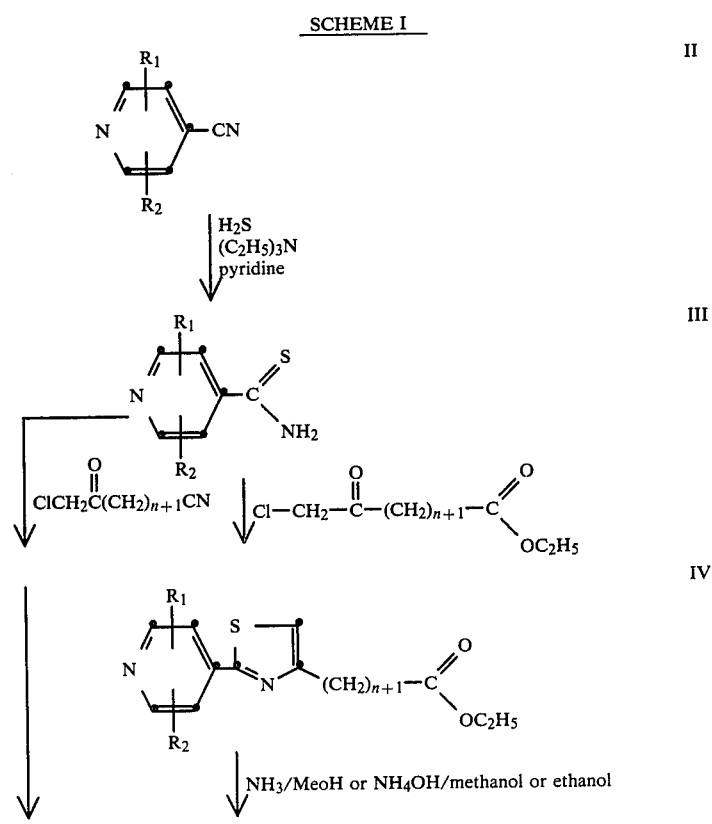

SCHEME I
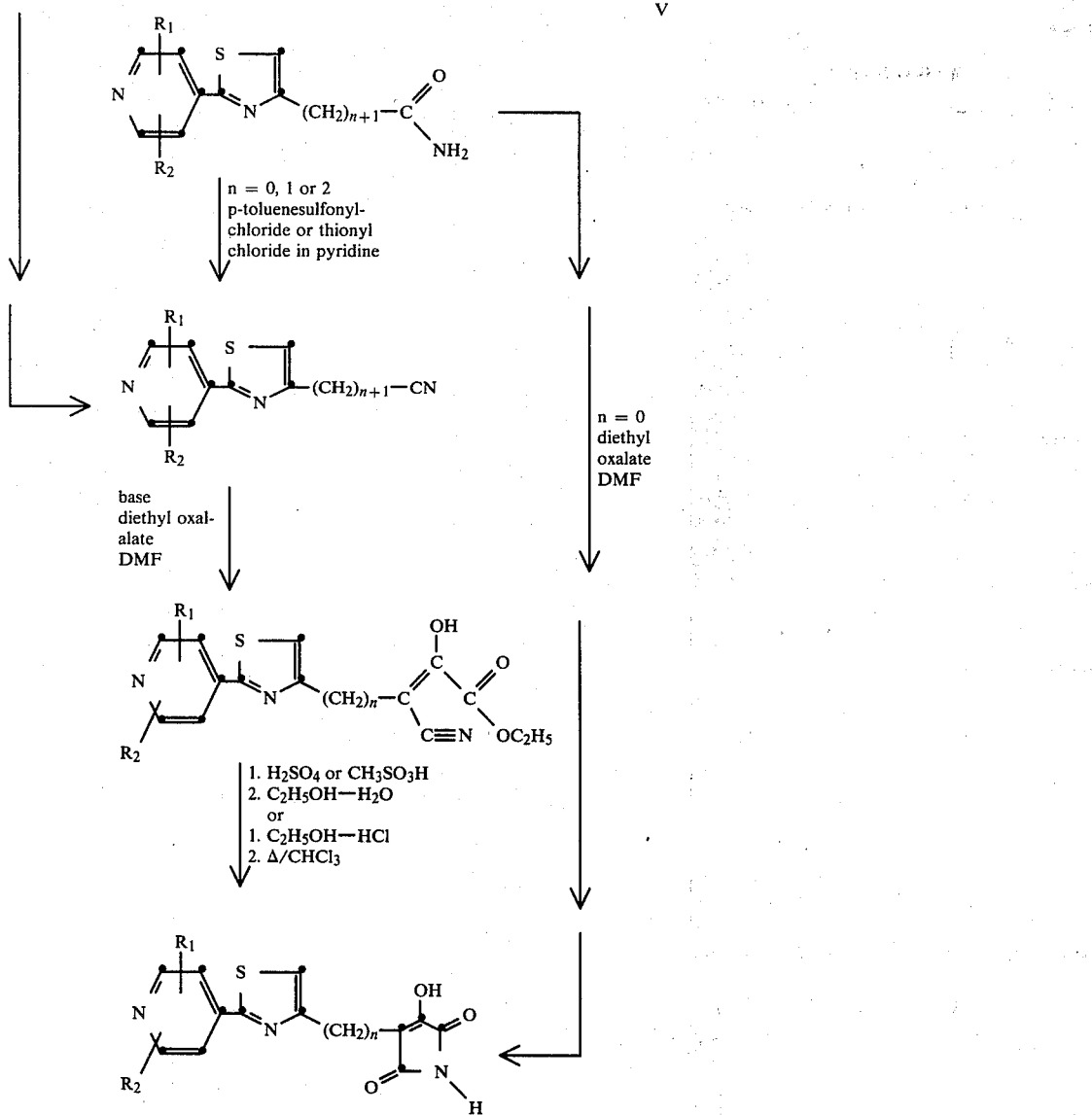
SCHEME II
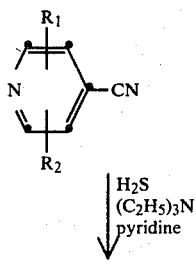
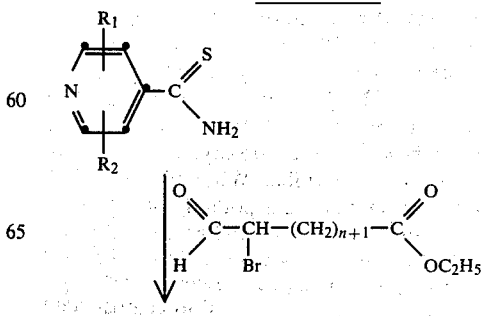

-continued
SCHEME II

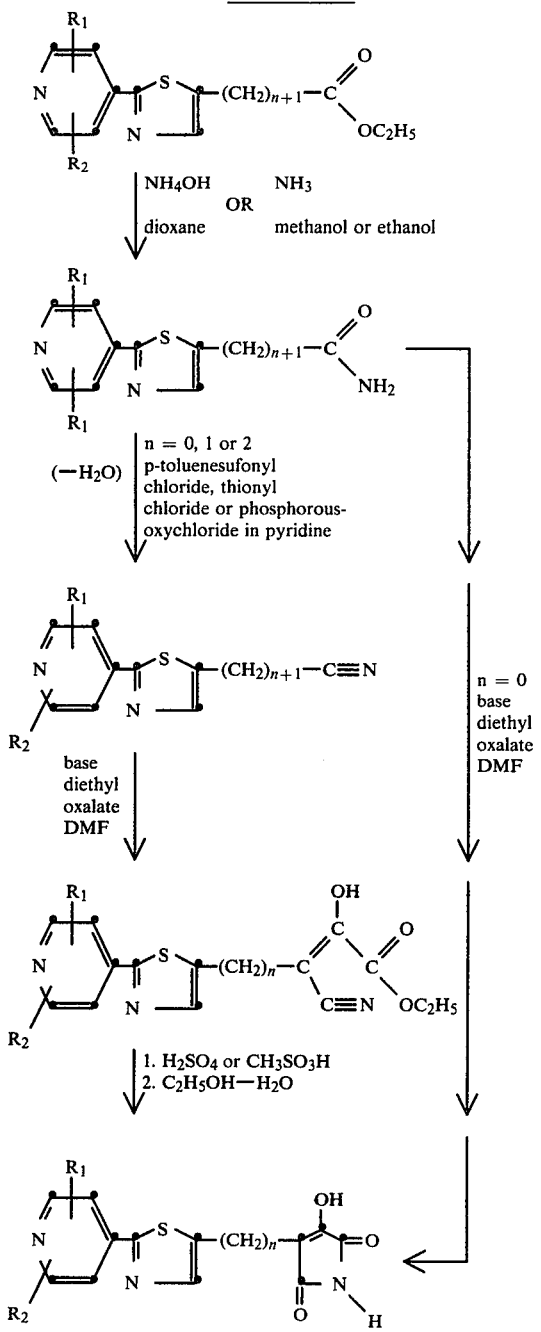

wherein
R$_1$ and R$_2$ are as defined above.

The compounds (I) wherein the heterocyclic substituent is at the 2-position of the thiazole ring are prepared generally by the method of Fairfull, Lowe and Peak, *J. Chem. Soc.*, 742 (1952). The nitrile (II), prepared by known methods, is reacted with excess hydrogen sulfide gas in the presence of excess triethylamine in a basic organic solvent such as pyridine. When the reaction is complete, the reaction mixture is poured into ice-water and the thiobenzamide (III) collected by filtration.

When n=0 the ethyl 4-thiazolylacetates (IV) are prepared by the classic Hantzsch procedure using the thiobenzamide (III) and ethyl 4-chloroacetoacetate.

When n=1 or 2 the homologous chloro- or bromomethyl ketones are utilized.

Stirring the esters (IV) in concentrated ammonium hydroxide and dioxane or ammonia in methanol or ethanol for varying lengths of time, and temperature yield the corresponding amides (V).

Preparation of the pyrrolinediones from the amides (V) is accomplished by two different routes.

1. When n=0 the amides react with diethyl oxalate in a solvent such as DMF in the presence of strong base (generally alkali metal alkoxide) under an inert atmosphere. Acidification provides the desired hydroxypyrrolinedione derivative.

2. When n=0, 1 or 2, the intermediate amide is converted to the nitrile by dehydration using prior art procedures (e.g. thionyl chloride in DMF or pyridine, or p-toluenesulfonyl chloride in pyridine or DMF). The nitrile is reacted with diethyl oxalate and strong base (alkali metal alkoxide) in a solvent such as DMF or toluene. The resulting 3-cyano-2-ketoacid ethyl ester is converted to the desired 3-hydroxy-3-pyrroline-2,5-dione derivative by dissolving in sulfuric or methanesulfonic acid, allowing the mixture to stand at room temperature overnight, and then pouring into ethanol containing 5–10% water.

Alternatively, the 3-cyano-2-ketoacid ethyl ester intermediate may be converted to the iminoether using cold ethanolic hydrogen chloride for 20–48 hours. The iminoether hydrochloride on heating in refluxing chloroform is converted to the hydroxypyrrolinedione derivative.

For compounds of this invention wherein the hydroxypyrrolinedione moiety is attached at the 5-position of the thiazole ring, the above procedures are followed with the exception that for the thiazole ring-forming step there is utilized instead of the χ-haloketone, the isomeric χ-halo aldehydic ester intermediate. For example, in place of 4-chloroacetoacetic ethyl ester, 4-oxo-3-bromobutyric acid ethyl ester is employed.

The following examples, given by way of illustration and not to be construed as limiting, further clarify the invention.

EXAMPLE 1

General Method for the Preparation of 3-Hydroxy-4-substituted-3-pyrroline-2,5-diones from Thiazoleacetamide Intermediates A mixture of the substituted acetamide (10 mmole), diethyl oxalate (1.533 g, 10.5 mmole) and dry dimethylformamide (20 ml) is stirred under nitrogen or argon and cooled in an ice-bath. Potassium t-butoxide (2.464 g, 22 mmole) is added in two equal portions 15 minutes apart and the reaction mixture is stirred for about 30 minutes in the ice-bath and then at room temperature overnight. The reaction mixture is poured into ice-water (100 ml). If the potassium salt of the product dissolves, the aqueous mixture is extracted with ethyl acetate (2×35 ml) and then acidified with 6 N hydrochloric acid in order to precipitate the product. The product is either collected by filtration or by extraction with ethyl acetate.

If the potassium salt is not soluble when the reaction mixture is quenched in ice-water, then it is necessary to acidify the resulting suspension and collect the product by filtration. The crude product is generally less pure when obtained in this way.

Compounds may be solvated after recrystallization (with either DMF, dioxane, isopropanol or acetonitrile) and require drying at 110° C./0.05 Torr in order to remove the solvate.

EXAMPLE 2

Preparation of
3-Hydroxy-4-[2-(4-pyridyl)thiazol-5-yl]-3-pyrroline-2,5-dione

Pyridine-4-thioamide (1.38 g, 0.01 mole) and 3-bromo-4-oxobutyric acid ethyl ester (3.1 g., 0.015 mole) in ethanol (50 ml) are heated at reflux for six hours. After cooling the solvent is evaporated and the residue is neutralized with sodium bicarbonate solution and then extracted with chloroform (300 ml.). The chloroform solution is washed with water, dried with (MgSO$_4$) and evaporated to yield crude 2-(4-pyridyl)-thiazole-5-acetic acid ethyl ester. Purification is carried out by dissolving in acetone and adding petroleum ether to induce crystallization. When this ester intermediate is treated with methanol solution saturated with ammonia gas (25 ml./g. of ester) for 3 days at room temperature 2-(4-pyridyl)thiazol-5-ylacetamide is obtained after partial evaporation of the methanol. Purification is carried out by recrystallization from ethanol. When the amide is treated according to the procedure in Example 1, there is obtained 3-hydroxy-4-[2-(4-pyridyl)thiazol-5-yl]-3-pyrroline-2,5-dione.

When the above procedure is carried out starting with 3-chloro or 3-bromopyridine-4-thioamide, but substituting 4-chloro-3-oxobutyric acid ethyl ester for the 3-bromo-4-oxobutyric acid ethyl ester, there are obtained 3-hydroxy-4-[2-(3-chloro-4-pyridyl)thiazol-4-yl]-3-pyrroline-2,5-dione and 3-hydroxy-4-[3-bromo-4-pyridyl)thiazol-4-yl]-3-pyrroline-2,5-dione respectively.

EXAMPLE 3

3-Hydroxy-4-[2-(4-pyridyl)thiazol-4-yl]-3-pyrroline-2,5-dione

When pyridine-4-thioamide is reacted with 6-chloro-5-oxohexanenitrile, according to the procedure of Example 2 (in place of 3-bromo-4-oxobutyric acid ethyl ester) there is obtained 4-[2-(4-pyridiyl)thiazol-4-yl]-butanenitrile. To a solution of this nitrile (2.29 g., 0.01 mole) in dimethylformamide (30 ml.) is added diethyloxalate (1.74 g., 0.012 mole), and potassium t-butoxide (2.48 g., 0.022 mole). The mixture is stirred overnight. Following evaporation under vacuum to one-half volume, chloroform (500 ml.) is added plus water (200 ml.), and the mixture acidified with conc. HCl to pH 2–3. The chloroform is separated, washed well with water, and evaporated to yield 2-oxo-3-cyano-5-[2-(4-pyridyl)thiazol-5-yl]pentanoic acid ethyl ester. The ester (3.24 g., 0.01 mole) is dissolved in methanesulfuric acid (30 ml.) and stirred for 24 hours. To the acidic mixture is added 80% ethanol-water. After standing for 2 hours, the ethanol is removed under vacuum. The residual aqueous mixture is neutralized with pyridine to pH 2–3, and the title product obtained on filtration.

EXAMPLE 4

2-[2-(4-Pyridyl)thiazol-4-yl]acetonitrile

To 2-[2-(4-pyridyl)thiazol-4-yl]acetamide (2.19 g., 0.01 mole) in pyridine (30 ml.) is added gradually p-toluenesulfuryl chloride (1.91 g., 0.01 mole). After stirring for one hour the mixture is poured into excess ice-water to give the title compound.

The physical constants of certain intermediates and end-product hydroxypyrrolinediones of this invention are tabulated below:

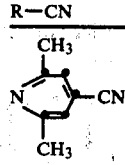
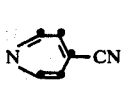
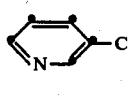

| R—CN | | Calc. | Fd. | | Calc. | Fd. | | Calc. | Fd. |
|---|---|---|---|---|---|---|---|---|---|
| 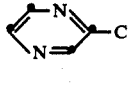 | N | 8.96 | 8.89 | N | 16.99 | 16.86 | N | 13.95 | 14.22 |
| | C | 53.75 | 53.71 | C | 58.28 | 58.49 | C | 55.80 | 55.60 |
| | H | 5.48 | 5.30 | H | 5.30 | 5.28 | H | 3.68 | 3.64 |
| | Cl | 11.33 | 11.26 | | | | | | |
| | MP 94–96° C. | | | MP 208–210° C. | | | MP 288° C. | | |
| 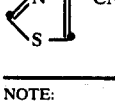 | N | 11.28 | 11.43 | N | 19.17 | 18.87 | N | 15.38 | 15.66 |
| | C | 58.04 | 58.29 | C | 54.78 | 54.72 | C | 52.74 | 52.57 |
| | H | 4.87 | 4.91 | H | 4.14 | 4.26 | H | 2.58 | 2.71 |
| | | | | MP 197–199° C. | | | MP 290° C. (dec.) | | |
| 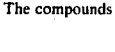 | N | 9.84 | 10.04 | N | 19.17 | 19.03 | N | 15.38 | 15.62 |
| | C | 50.61 | 50.43 | C | 54.78 | 54.78 | C | 52.74 | 52.97 |
| | H | 4.60 | 4.62 | H | 4.14 | 4.20 | H | 2.58 | 2.44 |
| | MP 123–125° C. | | | MP 175–177° C. | | | MP 269–270° C. | | |
| | Oil | | | N | 25.44 | 25.38 | N | 20.43 | 20.44 |
| | | | | C | 49.08 | 49.07 | C | 48.17 | 48.05 |
| | | | | H | 3.66 | 3.61 | H | 2.21 | 2.24 |
| | | | | MP 169–171° C. | | | MP 289–291° C. (dec.) | | |
| | N | 11.02 | 11.12 | N | 18.65 | 18.53 | N | 15.05 | 15.21 |
| | C | 47.22 | 47.46 | C | 42.65 | 42.71 | C | 43.00 | 42.81 |
| | H | 3.96 | 3.95 | H | 3.13 | 3.08 | H | 1.80 | 1.92 |
| | MP 88–90° C. | | | MP 175–177° C. | | | MP 279–280° C. (dec.) | | |

NOTE:
The compounds of this invention may also be termed 3-(substituted thiazolyl)-4-hydroxy-3-pyrroline-2,5-dione derivatives.

Included within the scope of the invention are the pharmaceutically acceptable salts of formula (I) compounds. The compounds of formula (I) are strong organic acids with a pKa in the range 2-4. Thus salts are readily formed with the usual inorganic cations such as sodium, potassium and ammonium. Salts with organic amines such as trimethylamine, triethylamine, n-butylamine and the like are also very stable. The neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt.

The compounds of formula (I) are utilized for the stated utilities by formulating them in a composition such as tablet, capsule or elixir for oral administration. Sterile solutions or suspensions can be used for parenteral administration. About 10 to 200 mg of a compound of formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose will be in the 30 to 2000 mg range, and preferably in the range of 50 mg to 1000 mg.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose or lactose; a flavoring agent such as peppermint, oil of wintergreen or cherry. When the dosage unit form is a capsule, it may contain in addition to materials of the above type a liquid carried such as a fatty oil. Various other materials may be present as coating or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

What is claimed is:

1. The compounds having the structure:

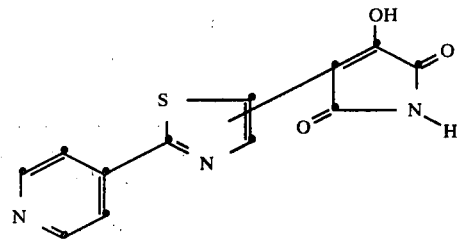

2. The compound having the structure:

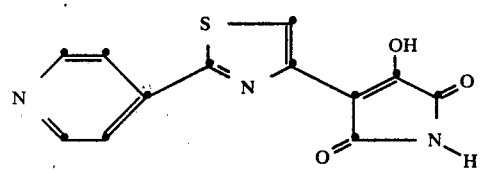

3. The compound having the structure:

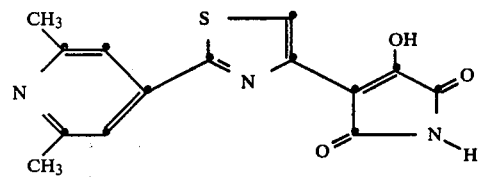

4. The compound having the structure:

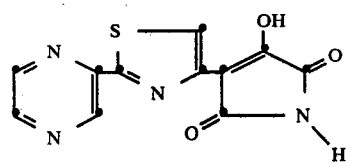

5. The compound having the structure:

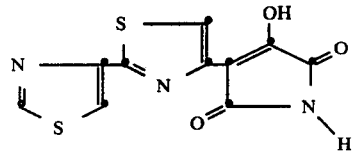

* * * * *